United States Patent
Hiraga et al.

(10) Patent No.: US 12,349,870 B2
(45) Date of Patent: Jul. 8, 2025

(54) ENDOSCOPE SYSTEM, CONTROL APPARATUS, AND GAS FEEDING CONTROL METHOD

(71) Applicant: OLYMPUS CORPORATION, Tokyo (JP)

(72) Inventors: Kunitoshi Hiraga, Tama (JP); Goki Numata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 712 days.

(21) Appl. No.: 17/500,469

(22) Filed: Oct. 13, 2021

(65) Prior Publication Data

US 2022/0031153 A1   Feb. 3, 2022

Related U.S. Application Data

(63) Continuation of application No. PCT/JP2019/016359, filed on Apr. 16, 2019.

(51) Int. Cl.
*A61B 1/015* (2006.01)
*A61B 1/00* (2006.01)
(Continued)

(52) U.S. Cl.
CPC .......... *A61B 1/015* (2013.01); *A61B 1/00006* (2013.01); *A61B 1/00068* (2013.01);
(Continued)

(58) Field of Classification Search
CPC ........... A61B 1/015; A61B 1/12; A61B 1/126; A61B 1/127; A61B 1/128; A61B 17/3474;
(Continued)

(56) References Cited

U.S. PATENT DOCUMENTS 8,231,523 B2 * 7/2012 Uesugi ............... A61B 1/00068
  604/23
2006/0030751 A1 * 2/2006 Uesugi ............... A61B 1/00068
  600/101
(Continued)

FOREIGN PATENT DOCUMENTS

JP   2006-167299 A   6/2006
JP   2011-212134 A   10/2011
(Continued)

OTHER PUBLICATIONS

International Search Report dated Jul. 16, 2019 received in PCT/JP2019/016359.

Primary Examiner — Ryan N Henderson
(74) Attorney, Agent, or Firm — Scully, Scott, Murphy & Presser, P.C.

(57) ABSTRACT

An endoscope system includes a gas feeding apparatus that feeds carbon dioxide, and a light source apparatus provided with an air pump for supplying air. The endoscope system feeds the carbon dioxide or the air from a distal end of an endoscope when a gas/liquid feeding button provided to the endoscope is operated. The endoscope system includes a pressure meter and a processor. The pressure meter is provided inside the gas feeding apparatus and configured to detect a pressure of the carbon dioxide. The processor is configured to perform control for stopping feeding of the air by the air pump when determining that, after the carbon dioxide is fed by an operation of the gas/liquid feeding button, the pressure of the carbon dioxide detected by the pressure meter reaches a predetermined threshold.

18 Claims, 11 Drawing Sheets

(51) Int. Cl.
*A61B 17/34* (2006.01)
*A61M 13/00* (2006.01)

(52) U.S. Cl.
CPC ....... *A61B 1/00119* (2013.01); *A61B 17/3474* (2013.01); *A61M 13/00* (2013.01); *A61M 13/003* (2013.01); *A61M 13/006* (2014.02); *A61M 2202/0225* (2013.01)

(58) Field of Classification Search
CPC .............. A61M 13/00; A61M 2202/02; A61M 2202/0225; A61M 13/003; A61M 13/006
See application file for complete search history.

(56) References Cited

U.S. PATENT DOCUMENTS

| | | | | |
|---|---|---|---|---|
| 2007/0238929 | A1* | 10/2007 | Aizenfeld | A61B 1/015 600/158 |
| 2007/0244363 | A1* | 10/2007 | Sano | A61M 13/003 600/118 |
| 2011/0245606 | A1* | 10/2011 | Hayashi | A61B 1/0661 600/109 |
| 2011/0245607 | A1* | 10/2011 | Hayashi | A61B 1/015 600/109 |
| 2012/0016293 | A1* | 1/2012 | Hayashi | A61B 1/126 604/24 |
| 2014/0066839 | A1* | 3/2014 | Torisawa | A61M 13/003 604/26 |
| 2015/0080757 | A1* | 3/2015 | Torisawa | A61B 1/31 600/560 |
| 2015/0250958 | A1* | 9/2015 | Hayashi | A61M 39/22 604/26 |
| 2015/0265784 | A1* | 9/2015 | Lampert | A61B 1/00006 604/26 |
| 2015/0290403 | A1* | 10/2015 | Torisawa | A61B 17/3474 604/26 |
| 2015/0290404 | A1* | 10/2015 | Torisawa | A61B 1/015 604/26 |
| 2017/0252505 | A1* | 9/2017 | Wu | A61M 1/3667 |
| 2019/0105451 | A1* | 4/2019 | Levêque | A61M 16/044 |
| 2021/0052148 | A1* | 2/2021 | Hong | A61B 1/00068 |

FOREIGN PATENT DOCUMENTS

| | | |
|---|---|---|
| JP | 2011-244937 A | 12/2011 |
| JP | 2012-035060 A | 2/2012 |
| JP | 2014094238 A | 5/2014 |
| JP | 5611637 B2 | 10/2014 |
| JP | 2016-209345 A | 12/2016 |

* cited by examiner

ENDOSCOPE SYSTEM, CONTROL APPARATUS, AND GAS FEEDING CONTROL METHOD

CROSS-REFERENCE TO RELATED APPLICATION

This application is a continuation application of PCT/JP2019/016359 filed on Apr. 16, 2019, the entire contents of which are incorporated herein by this reference.

BACKGROUND OF THE INVENTION

1. Field of the Invention

The present invention relates to an endoscope system including a gas feeding apparatus configured to feed carbon dioxide and an air supplying apparatus configured to supply air, and also relates to a control apparatus and a gas feeding control method.

2. Description of the Related Art

When an examination or a treatment is performed with an endoscope, gas is supplied from a gas feeding conduit provided in the endoscope into a body cavity in order to secure a field of view of the endoscope and an operation region for a treatment instrument. Air or carbon dioxide is used as gas to be fed into a body cavity. Carbon dioxide has a higher bioabsorbability than air, which provides an advantage that a patient feels less bloating.

Generally, an air pump provided to a light source apparatus is used for feeding air into a body cavity. A gas feeding apparatus including a gas container filled with carbon dioxide is used for feeding carbon dioxide into a body cavity.

In addition, some endoscope systems include both a light source apparatus and a gas feeding apparatus and enable an operator to selectively use air or carbon dioxide. When using such endoscope systems, if both air and carbon dioxide are simultaneously fed, excessive amount of gas is supplied into a body cavity. Therefore, an operator has to select gas to be used and perform switching of the gas to be fed.

When performing such switching of the gas to be used, the operator has to operate a feeding start/stop button for air or a feeding start/stop button for carbon dioxide. Such a button operation is a burden on the operator.

Japanese Patent No. 5611637 discloses a medical gas feeding system. In the medical gas feeding system, in order to reduce the above-described burden of switching operation on the operator, when detecting operation of the operation button of the gas feeding apparatus, the control section switches the air pump of the light source apparatus, which has been already operated, to a non-operating state.

SUMMARY OF THE INVENTION

An endoscope system according to one aspect of the present invention includes a gas feeding apparatus that feeds carbon dioxide, and an air supplying apparatus that supplies air, and the endoscope system feeds the carbon dioxide or the air from a distal end of an endoscope, when a predetermined operation member provided to the endoscope is operated. The endoscope system includes: a gas state detector provided inside the gas feeding apparatus, the gas state detector being configured to detect a state of the carbon dioxide, and a processor configured to perform control for stopping feeding of the air by the air supplying apparatus, when determining that, after the carbon dioxide is fed by the operation of the operation member, the state of the carbon dioxide detected by the gas state detector reaches a predetermined threshold.

A control apparatus according to one aspect of the present invention includes a processor configured to control feeding of carbon dioxide by a gas feeding apparatus and feeding of air by an air supplying apparatus. The processor is configured to: detect a state of the carbon dioxide fed from the gas feeding apparatus; and perform control for stopping the feeding of the air by the air supplying apparatus, when determining that, after the carbon dioxide is fed by an operation of an operation member provided to an endoscope, the detected state of the carbon dioxide reaches a predetermined threshold.

A gas feeding control method according to one aspect of the present invention is a gas feeding control method using a gas feeding apparatus that feeds gas into a body cavity and an air supplying apparatus that supplies air into the body cavity. The method includes: detecting a state of carbon dioxide fed from the gas feeding apparatus; and performing control for stopping feeding of the air by the air supplying apparatus, when determining that, after the carbon dioxide is fed by an operation of an operation member provided to an endoscope, the detected state of the carbon dioxide reaches a predetermined threshold.

DETAILED DESCRIPTION OF THE PREFERRED EMBODIMENT(S)

Hereinafter, embodiments of the present invention will be described with reference to drawings.

First Embodiment

Figure 1:
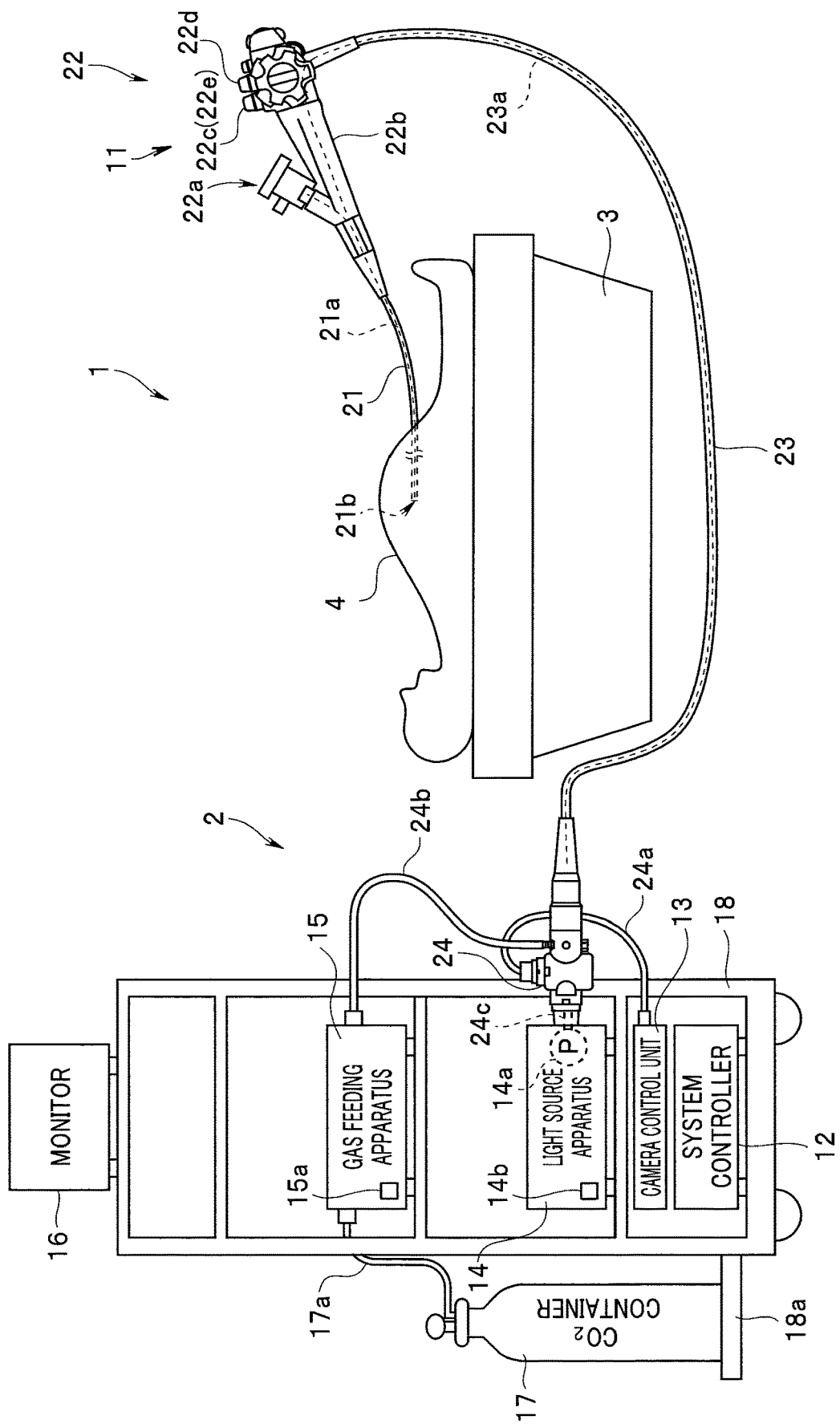
FIG. 1 is a configuration view of a medical system according to a first embodiment of the present invention.

FIG. 1 is a configuration view of a medical system according to the first embodiment. A medical system 1 is a system for performing an examination or a treatment of a subject 4 as a patient on a bed 3 by using an endoscope system 2.

The endoscope system 2 includes an endoscope 11, a system controller 12, a camera control unit 13, a light source apparatus 14, a gas feeding apparatus 15, a monitor 16, a carbon dioxide container 17.

The system controller 12, the camera control unit 13, the light source apparatus 14, the gas feeding apparatus 15, and the monitor 16 are placed on a cart 18 which is a placing table. The carbon dioxide container 17 is placed on an extending part 18a extended from the cart 18. The carbon dioxide container 17 is connected to the gas feeding apparatus 15 by a connecting tube 17a.

The endoscope 11 includes an elongated insertion portion 21, an operation portion 22 connected to a proximal end of the insertion portion 21, and a universal cable 23 extended from the operation portion 22, and a connector 24 provided at a distal end portion of the universal cable 23. The connector 24 includes a cable 24a connected to the camera control unit 13, and a gas feeding tube 24b connected to the gas feeding apparatus 15.

The endoscope 11 includes, at a distal end portion of the insertion portion 21, an observation window and an illumination window, which are not shown. On a rear side of the observation window, an image pickup device such as a CMOS image sensor is provided. The light from the subject is incident through the observation window and an image of the light is formed on an image pickup surface of the image pickup device. The image pickup device is configured to photoelectrically convert the image of an inside of the subject, which is formed on the image pickup surface, and output an image pickup signal. The image pickup signal is supplied to the camera control unit 13 by a signal line inserted through the insertion portion 21, the operation portion 22, the universal cable 23, and the cable 24a. The camera control unit 13 generates an endoscopic image based on the received image pickup signal, to output the generated endoscopic image to the monitor 16.

On a rear side of the illumination window disposed at the distal end of the insertion portion 21, a distal end surface of an elongated light guide, not shown, is disposed. The light guide is inserted through the insertion portion 21, the operation portion 22, and the universal cable 23. A proximal end surface of the elongated light guide is disposed near a light source in the light source apparatus 14 through the connector 24. The light from the light source of the light source apparatus 14 passes through the light guide and is emitted from the distal end of the insertion portion 21, to illuminate the inside of the subject. Reflected light of the illumination light is received by the image pickup device. An operator can perform a desired examination or a desired treatment, while viewing the endoscopic image displayed on the monitor 16.

The system controller 12 controls operation of the entirety of the endoscope system 2, and various apparatuses, such as the camera control unit 13, connected to the system controller 12. The system controller 12 is connected to the camera control unit 13 through a signal cable, not shown.

The camera control unit 13 is connected to the monitor 16 by a cable, not shown. The camera control unit 13, for example, generates an endoscopic image and outputs an image signal of the endoscopic image to the monitor 16. Furthermore, the system controller 12 is connected to the light source apparatus 14 and the gas feeding apparatus 15 through a plurality of signal lines to be described later.

In addition, the light source apparatus 14 includes an air pump 14a. Air from the air pump 14a can be supplied to a gas feeding channel 23a in the universal cable 23 through an air flow path 24c (shown with a dotted line) provided in the connector 24. The light source apparatus 14 configures an air supplying apparatus for supplying air.

The gas feeding apparatus 15 discharges the carbon dioxide in the carbon dioxide container 17 to the gas feeding tube 24b. The carbon dioxide from the gas feeding apparatus 15 is supplied to the connector 24 through the gas feeding tube 24b. A gas passage is formed in the connector 24. The gas passage is configured to allow the gas feeding tube 24b and the gas feeding channel 23a in the universal cable 23 to communicate with each other.

The gas feeding channel 23a in the universal cable 23 passes through the operation portion 22 to be communicated with a gas feeding path 21a in the insertion portion 21. The insertion portion 21 includes, inside thereof, a liquid feeding path, not shown. A distal end of the gas feeding path 21a is connected to the liquid feeding path, to thereby form a gas/liquid feeding conduit at the distal end of the insertion portion 21. A distal end of the gas/liquid feeding conduit is connected to a nozzle disposed at the distal end of the insertion portion 21, so as to allow gas and liquid to be discharged from an opening 21b of the nozzle.

The operation portion 22 includes a gas/liquid feeding button 22c and a suction button 22d. When the operator closes a hole formed on the gas/liquid feeding button 22c, a gas feeding passage of the gas in the operation portion 22 is formed, to thereby enable the air from the light source apparatus 14 or the carbon dioxide from the gas feeding apparatus 15 to be supplied to the gas feeding path 21a. For example, a cylinder provided in the operation portion 22 includes an opening through which the air or the carbon dioxide flows in. When the operator closes the hole formed on the gas/liquid feeding button 22c, a flow path is formed. The flow path allows the air or the carbon dioxide to pass from the gas feeding channel 23a to the gas feeding path 21a, to be discharged from the opening 21b of the nozzle at the distal end of the insertion portion 21.

There is a case where a gas/liquid feeding button 22e is connected instead of the gas/liquid feeding button 22c. The gas/liquid feeding button 22e is configured to be able to be depressed in two stages. When the gas/liquid feeding button 22e is not depressed, the gas stops at the entrance of the gas/liquid feeding button 22e. When the gas/liquid feeding button 22e is depressed to the first stage, gas is fed, and when the gas/liquid feeding button 22e is further depressed to the second stage, liquid is fed.

Although not described in detail here, when the gas/liquid feeding button 22c is depressed, water from the liquid feeding path is discharged from the opening 21b of the nozzle at the distal end of the insertion portion 21, and when the suction button 22d is depressed, suction is performed from the opening 21b of the nozzle at the distal end of the insertion portion 21.

As described above, the endoscope system 2 includes the gas feeding apparatus 15 configured to feed carbon dioxide and the light source apparatus 14 which is the air supplying apparatus for supplying air. When the gas/liquid feeding button 22c, which is a predetermined operation member provided to the endoscope 11 is operated, carbon dioxide or air is fed from the distal end of the endoscope 11. Accordingly, the operator can feed gas into the body cavity of the subject by operating the gas/liquid feeding button 22c, to thereby be capable of ensuring the field of view of the endoscope.

Figure 2:
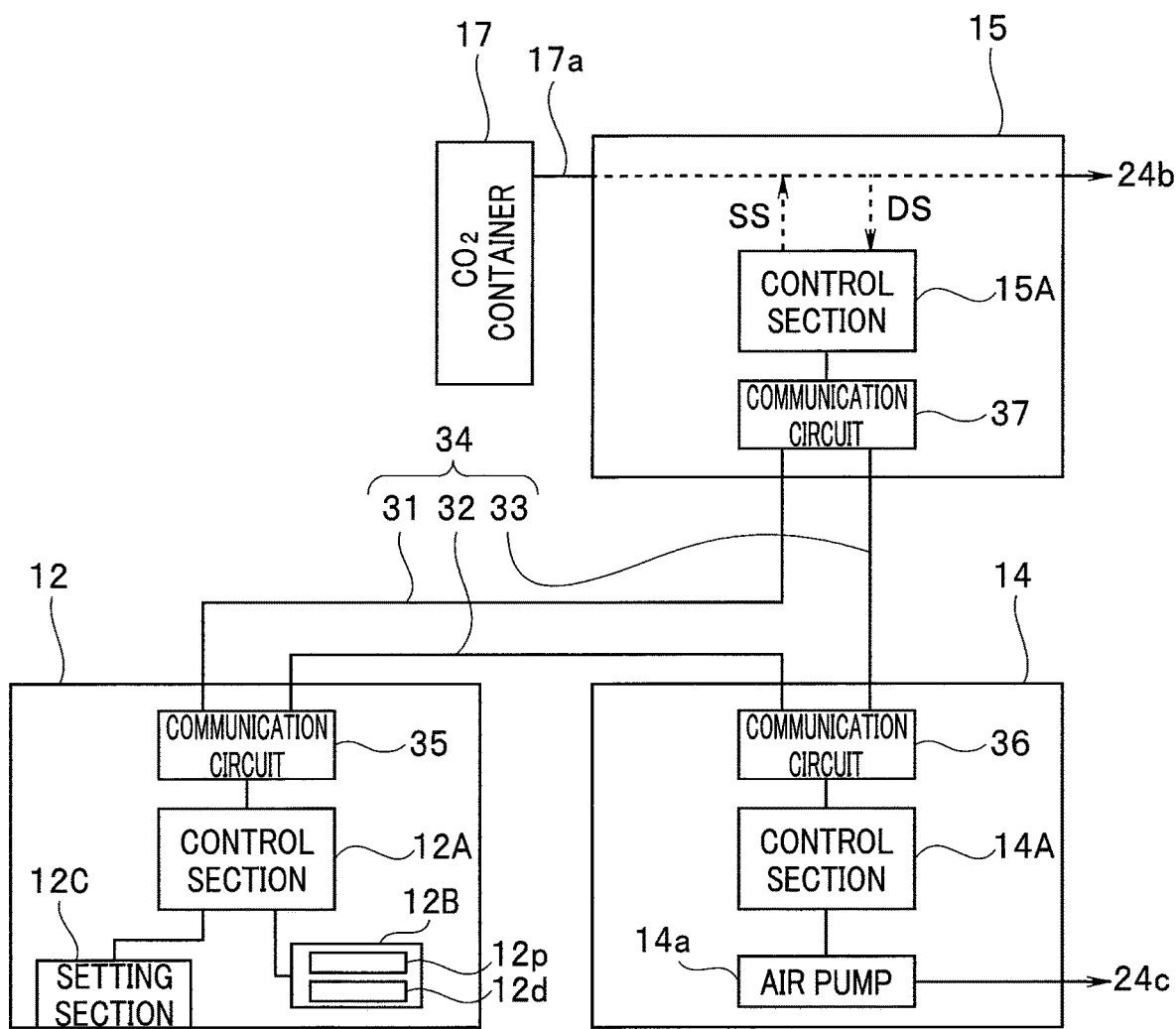
FIG. 2 is a block diagram showing a connecting relation of signal lines connecting a system controller, a light source apparatus, and a gas feeding apparatus that constitute an endoscope system, according to the first embodiment of the present invention.

FIG. 2 is a block diagram showing a connecting relation of signal lines connecting the system controller 12, the light source apparatus 14, and the gas feeding apparatus 15 that constitute the endoscope system 1. The system controller 12 and the gas feeding apparatus 15 are connected to each other through a communication line 31. The system controller 12 and the light source apparatus 14 are connected to each other through a communication line 32. The light source apparatus 14 and the gas feeding apparatus 15 are connected to each other through a communication line 33. The communication lines 31, 32, and 33 constitute a communication network 34. In the present embodiment, the communication network 34 is constituted of the communication lines 31, 32, and 33 formed in a ring shape, but may be another type of network such as a bus-shaped network. The system controller 12, the light source apparatus 14, and the gas feeding apparatus 15 are capable of communicating one another via the communication network 34.

The system controller 12 includes a control section 12A, a storage apparatus 12B, a setting section 12C, and a communication circuit 35. The communication lines 31, 32 are connected to the communication circuit 35. The system controller 12 includes various circuits, apparatuses, etc., for controlling the entirety of the endoscope system 1, as described above. However, illustration of such circuits, apparatuses, etc., are omitted in FIG. 2.

The storage apparatus 12B includes a program storage region 12p for storing various programs, and a data storage region 12d for storing various data. The program storage region 12p stores a stop control program 12x for performing later-described stop control of the air pump 14a of the light source apparatus 14. The data storage region 12d stores data of a threshold TH to be described later. The setting of the threshold TH can be changed by the setting section 12C. In other words, the setting section 12C configures a threshold setting section configured to set the predetermined threshold TH for the state of gas. The setting section 12C is a setting display device including a touch panel apparatus and a display apparatus, for example.

The control section 12A can perform communication with the light source apparatus 14 and the gas feeding apparatus 15 through the communication circuit 35. The control section 12A can receive various signals from the light source apparatus 14 and the gas feeding apparatus 15 and transmit control signals to the light source apparatus 14 and the gas feeding apparatus 15.

The light source apparatus 14 includes a control section 14A, a communication circuit 36, and the air pump 14a. The light source apparatus 14 includes various apparatuses such as the light source, a filter, and the like. However, illustration of such apparatuses is omitted in FIG. 2. When a power source switch 14b is turned on, the light source apparatus 14 turns on the air pump 14a to cause the air pump to operate. As a result, air is fed to the gas feeding channel 23a. In this state, if the operator closes the hole of the gas/liquid feeding button 22c, the air is fed from the opening 21b of the nozzle at the distal end of the insertion portion 21. Note that, in the case where the light source apparatus 14 is provided with an on/off switch for turning on and off the air pump 14a, in addition to the power source switch 14b, when the on/off switch is turned on after the power source switch 14b has been turned on, the air pump 14a is turned on. The control section 14A can perform communication with the system controller 12 and the gas feeding apparatus 15 through the communication circuit 36.

The gas feeding apparatus 15 includes a control section 15A and a communication circuit 37. The gas feeding apparatus 15 includes various apparatuses such as decompressors, a sensor, and the like, as will be described later. However, such apparatuses are not shown in FIG. 2. The control section 15A can perform communication with the system controller 12 and the light source apparatus 14 through the communication circuit 37.

The control section 15A outputs a control signal SS to a flow rate adjusting valve 43 configured to supply carbon dioxide, and transmits, in real time, a detection signal DS to the system controller 12 through the communication circuit 37. The detection signal DS is a signal from a sensor configured to detect the state of the carbon dioxide.

The control section 12A of the system controller 12 can generate a control signal for controlling the operation of the air pump 14a based on the received detection signal DS, and transmit the generated control signal to the light source apparatus 14.

Each of the control sections 12A, 14A, and 15A includes a processor. The processor includes a central processing unit (CPU), ROM, RAM, and the like, and implements various functions by reading programs stored in the ROM and the storage apparatus 12B, developing the read programs in the RAM, and executing the programs. The processor may be configured of a semiconductor device such as an FPGA (Field Programmable Gate Array), or a circuit such as an electronic circuit.

Figure 3:
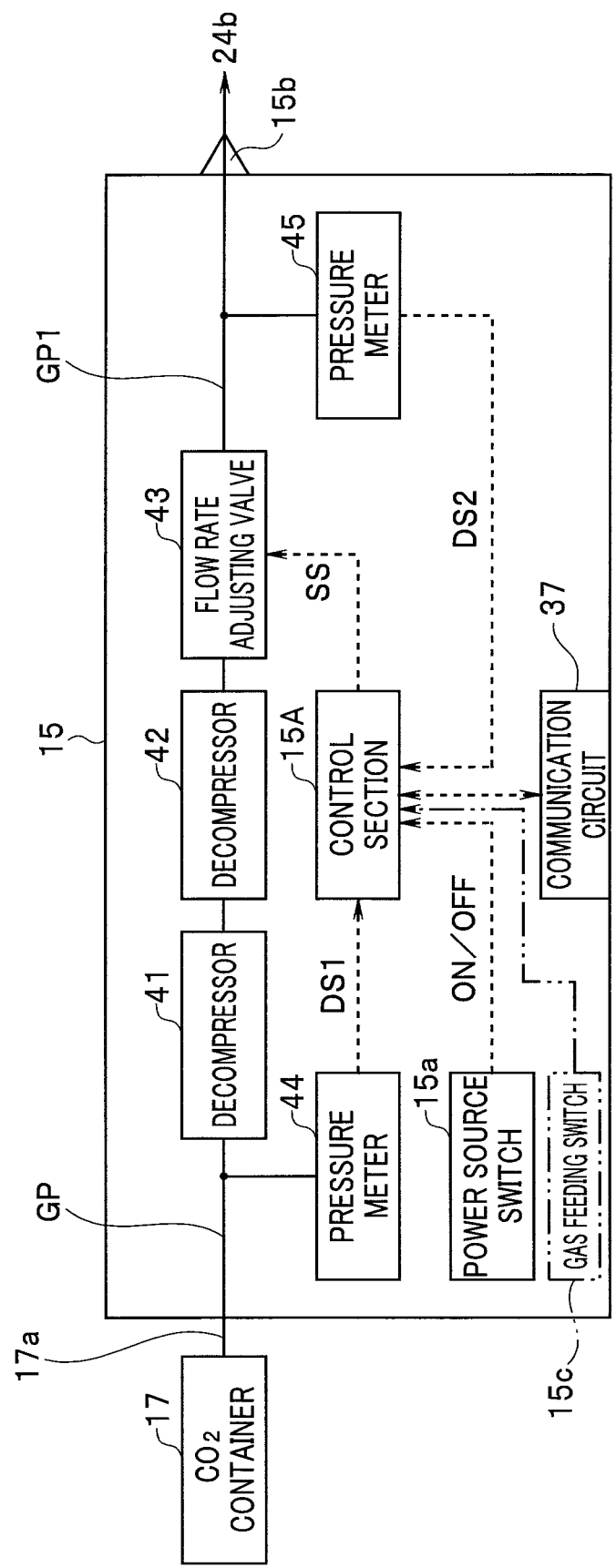
FIG. 3 is a block diagram showing a configuration of the gas feeding apparatus according to the first embodiment of the present invention.

FIG. 3 is a block diagram showing a configuration of the gas feeding apparatus 15. The gas feeding apparatus 15 includes a conduit GP to which the carbon dioxide from the carbon dioxide container 17 is supplied. The conduit GP is communicated with the connecting tube 17a and the gas feeding tube 24b, and allows the carbon dioxide from the carbon dioxide container 17 to be supplied to the gas feeding tube 24b connected to a gas feeding cap 15b. The conduit GP includes two decompressors 41, 42, and the flow rate adjusting valve 43 in this order from the side of the connecting tube 17a. The gas decompressed by the two decompressors 41, 42 is supplied to the flow rate adjusting valve 43.

The conduit GP includes, between the carbon dioxide container 17 and the decompressor 41, a pressure meter 44. The pressure meter 44 is configured to detect a pressure of the carbon dioxide in the carbon dioxide container 17 and output a detection signal DS1 of the detected pressure to the control section 15A. A pressure meter 45 is disposed between the flow rate adjusting valve 43 and the gas feeding tube 24b. The pressure meter 45, which is a gas state detector, is provided in a post-stage of the flow rate adjusting valve 43 configured to adjust the flow rate of the carbon dioxide to be fed from the gas feeding apparatus 15. The pressure meter 45 detects a pressure in a conduit GP1 located between the flow rate adjusting valve 43 and the gas feeding tube 24b, and outputs a detection signal DS2 of the detected pressure to the control section 15A. The pressure meter 45 is provided inside the gas feeding apparatus 15, and configures the gas state detector that detects the state of the carbon dioxide, i.e., the pressure of the carbon dioxide in the present embodiment.

The gas feeding apparatus 15 includes a power source switch 15a. The control section 15A is connected to the pressure meters 44, 45, and the flow rate adjusting valve 43. The control section 15A detects the on-state and the off-state of the power source switch 15a. When the power source switch 15a is turned on, the control section 15A controls the flow rate adjusting valve 43 based on the detection signal DS2 from the pressure meter 45, to supply the carbon dioxide from the carbon dioxide container 17 to the gas feeding tube 24b. Thus, the carbon dioxide is supplied from the gas feeding apparatus 15 to the gas feeding tube 24b.

As shown by the two-dot chain lines in FIG. 3, the gas feeding apparatus 15 may include a gas feeding switch 15c, in addition to the power source switch 15a. In that case, the gas feeding apparatus 15 is configured such that just turning on of the power source switch 15a does not cause the carbon dioxide to be supplied to the gas feeding tube 24b, but further turning on of the gas feeding switch 15c causes the flow rate adjusting valve 43 to open by the control section 15A, to thereby allow the carbon dioxide to be supplied from the gas feeding apparatus 15 to the gas feeding tube 24b.

(Working)

Next, description will be made on the stop control of the air pump in the above-described endoscope system. The stop control of the air pump is performed by the above-described stop control program 12x for performing the stop control of the air pump 14a.

The operator turns on the power source switches of respective devices to be used, before performing an examination and the like. When feeding air into a body cavity, the operator does not turn on the power source switch 15a of the gas feeding apparatus 15. When the operator wishes to feed carbon dioxide, instead of air, into the body cavity, the operator turns on the power source switch 15a.

Figure 4:
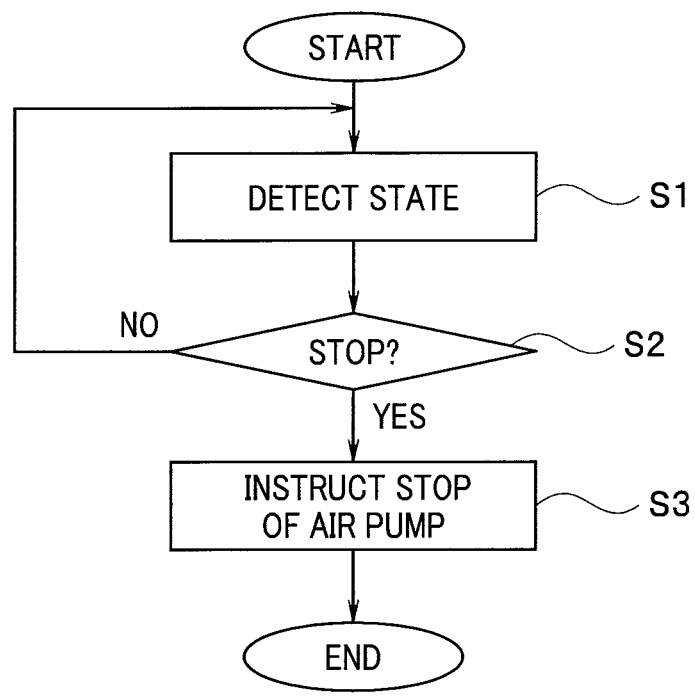
FIG. 4 is a flowchart showing an example of a flow of stop control of an air pump in a control section in the system controller, according to the first embodiment of the present invention.

FIG. 4 is a flowchart showing an example of a flow of the stop control of the air pump in the control section 12A. When the power source switch 15a of the gas feeding apparatus 15 is turned on, the control section 12A executes the stop control program 12x. The control section 12A performs state detection (Step (hereinafter abbreviated as S) 1). The state detection means, in the present embodiment, detection of a pressure P in the conduit GP1. S1 is receiving, from the gas feeding apparatus 15, pressure data of a pressure value detected by the pressure meter 45.

After the S1, the control section 12A performs determination on whether to stop the air pump 14a (S2). The determination on whether to stop the air pump 14a means, here, determining whether the pressure P in the conduit GP1 exceeds the predetermined threshold TH1. The operator inputs, in advance, the threshold TH1 from the setting section 12C, to set the threshold TH1. The threshold TH1 is stored in the data storage region of the storage apparatus 12B.

When the power source switch 15a is turned on, the flow rate adjusting valve 43 is opened, which leads to a rise in the pressure P in the conduit GP1. The conduit GP1 is a part of the conduit GP and located on the downstream side of the flow rate adjusting valve 43.

Figure 5:
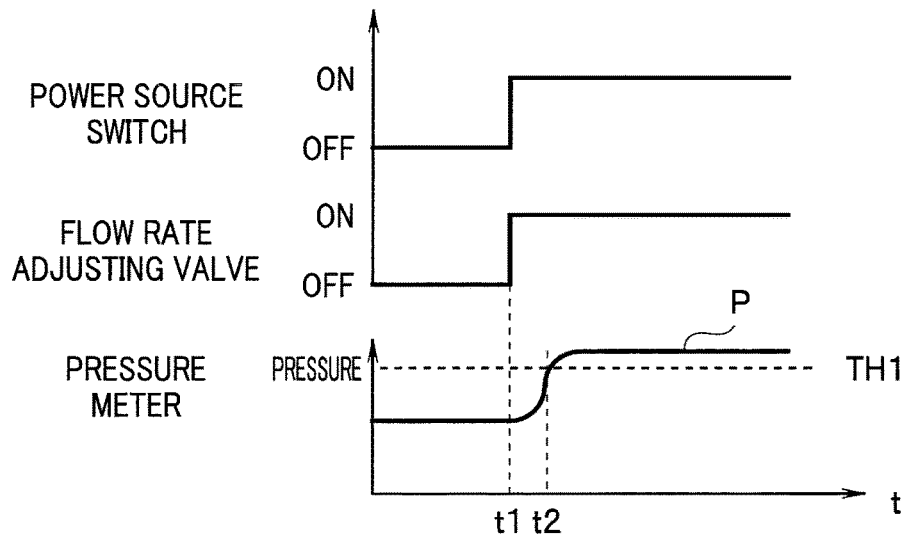
FIG. 5 is a graph showing a state of a power source switch of the gas feeding apparatus, a state of a flow rate adjusting valve, and a change in a pressure detected by a pressure meter, according to the first embodiment of the present invention.

FIG. 5 is a graph showing the state of the power source switch 15a of the gas feeding apparatus 15, the state of the flow rate adjusting valve 43, and the change in the pressure detected by the pressure meter 45. The horizontal axis in FIG. 5 shows a lapse of time. When the power source switch 15a is turned on at time t1, the flow rate adjusting valve 43 is turned on to be opened by the control section 15A. When the flow rate adjusting valve 43 is opened, the pressure in the conduit GP1 rises. As shown in FIG. 5, the pressure P detected by the pressure meter 45 rises after the time t1.

The control section 15A of the gas feeding apparatus 15 transmits, in real time, detection value data of the detection signal DS2 to the system controller 12 through the communication circuit 37. Accordingly, the control section 12A of the system controller 12 constantly monitors the received detection value data. In the S2, the control section 15A determines, based on the received detection value data, whether the pressure P in the conduit GP1 exceeds the predetermined threshold TH1.

The control section 12A instructs the stop of the air pump 14a when the pressure P detected by the pressure meter 45 exceeds the threshold TH1 (S3). In other words, the control section 12A transmits an operation stop command for stopping the operation of the air pump 14a to the light source apparatus 14. FIG. 5 shows that the pressure P in the conduit GP1 exceeds the predetermined threshold TH1 at the timing of the time t2. Since the pressure P exceeds the predetermined threshold TH1, the control section 12A transmits the operation stop command for stopping the operation of the air pump 14a from the communication circuit 35 to the light source apparatus 14 through the communication line 32.

When receiving the operation stop command, the control section 14A of the light source apparatus 14 outputs, to the air pump 14a, an off-signal for stopping the operation of the air pump 14a. As described above, when determining that the state of the carbon dioxide detected by the pressure meter 45, i.e., the pressure in the present embodiment, exceeds the predetermined threshold TH1, the control section 12A performs control for stopping the feeding of air by the air pump 14a that configures the air supplying apparatus.

In the case where the gas feeding apparatus 15 includes the gas feeding switch 15c, the control section 12A may transmit, to the light source apparatus 14, the operation stop command for stopping the operation of the air pump 14a, when the gas feeding switch 15c is turned on and the pressure P detected by the pressure meter 45 exceeds the threshold TH1. When receiving the operation stop command, the light source apparatus 14 stops the operation of the air pump 14a. In other words, when the pressure, which is the state of the carbon dioxide, exceeds the predetermined threshold TH1 and the gas feeding switch 15c of the gas feeding apparatus 15 is in the on-state, the control section 12A performs the control for stopping the feeding of the air by the air pump 14a.

In addition, in the case where the light source apparatus 14 further includes the on/off switch for turning on and off the air pump 14a, if the air pump 14a is operated when the light source apparatus 14 receives the operation stop command, the control section 14A stops the operation of the air pump 14a. If the air pump 14a is not operated when the light source apparatus 14 receives the operation stop command, the control section 14A does nothing.

However, in the case where the air pump 14a is not operated when the light source apparatus 14 receives the operation stop command, the control section 14A may bring the light source apparatus 14 into an operation inhibited state in which the air pump 14a is not allowed to operate even if the on/off switch is turned on later. In other words, the light source apparatus 14 is brought into a state which does not accept the turning on of the on/off switch. For example, the light source apparatus 14 sets, inside thereof, flag information indicating the operation inhibited state. When the light source apparatus 14 is in the operation inhibited state, the operator may be caused to perform an operation for confirming that the air pump 14a is allowed to operate so that the operator can bring the air pump 14a from the operation inhibited state into the operation enabled state in a case where the carbon dioxide concentration in the blood of the patient rises, for example.

Figure 6:
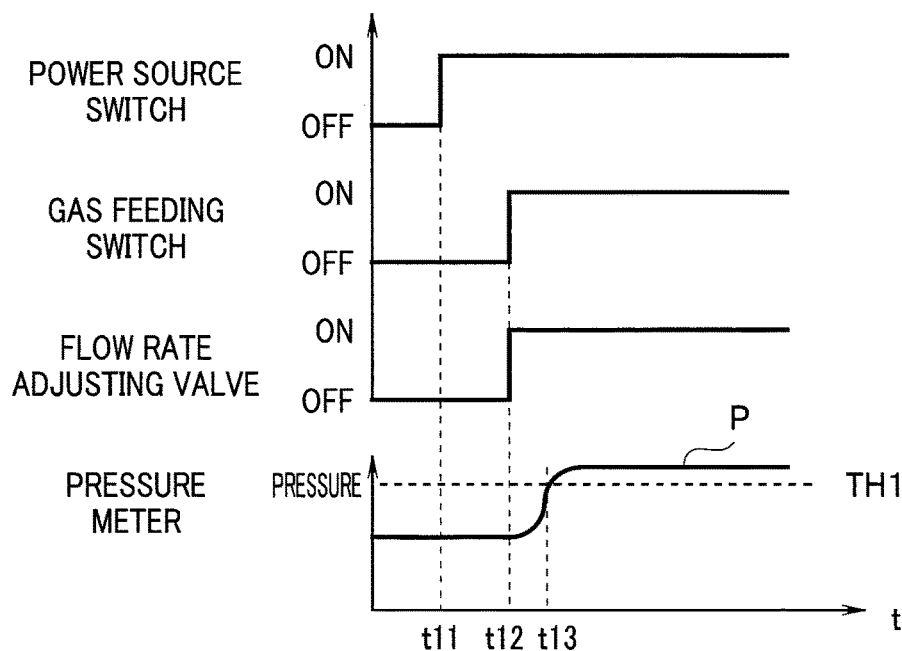
FIG. 6 is a graph showing the state of the power source switch of the gas feeding apparatus, a state of a gas feeding switch, the state of the flow rate adjusting valve, and a change in the pressure detected by the pressure meter, according to the first embodiment of the present invention.

FIG. 6 is a graph showing the state of the power source switch 15a of the gas feeding apparatus 15, the state of the gas feeding switch 15c, the state of the flow rate adjusting valve 43, and the change in the pressure detected by the pressure meter 45. The horizontal axis in FIG. 6 shows a lapse of time. After the power source switch 15a has been turned on at time t11, when the gas feeding switch 15c is turned on at time t12, the flow rate adjusting valve 43 is turned on to be opened by the control section 15A. When the flow rate adjusting valve 43 is opened, the pressure in the conduit GP1 rises. As shown in FIG. 6, the pressure P detected by the pressure meter 45 rises after time t13.

The control section 12A can determine that the gas feeding switch 15c of the gas feeding apparatus 15 is turned on by performing communication with the gas feeding apparatus 15 to acquire information on the state of the gas feeding switch 15c via the communication.

As described above, the control section 12A executes processing for stopping the operation of the air pump 14a at the timing of the time t2 (or t13) when the pressure P exceeds the predetermined threshold TH1.

Note that, in the present embodiment, the control section 12A of the system controller 12 receives the detection signal of the pressure meter 45 from the gas feeding apparatus 15, to transmit the operation stop command for stopping the operation of the air pump 14a to the light source apparatus 14. However, the control section 15A of the gas feeding apparatus 15 may transmit the operation stop command directly to the light source apparatus 14.

Furthermore, the control section 14A of the light source apparatus 14 may receive the detection value data of the pressure meter 45 from the gas feeding apparatus 15, to determine whether the pressure exceeds the threshold TH1, and may stop the operation of the air pump 14a.

The transmission processing of the detection value data of the pressure detected by the pressure meter 45 in the gas feeding apparatus 15 is executed by software processing or a hardware circuit in the control section 15A. The pressure monitoring processing of the pressure meter 45 and the transmission processing of the operation stop command for the air pump 14a in the system controller 12 are also executed by software processing or a hardware circuit in the control section 15A.

As described above, in the case where the operator turns on the power source switch 15a in order to use carbon dioxide for gas feeding into the body cavity, if the pressure P detected by the pressure meter 45 exceeds the predetermined threshold TH1, the operation of the air pump 14a of the light source apparatus 14 is stopped. Such a configuration prevents an excessive amount of gas from being supplied into the body cavity.

Normally, the pressure in the conduit GP1 of the conduit GP rises due to the carbon dioxide fed from the gas feeding apparatus 15. However, if the sufficient amount of gas does not remain in the carbon dioxide container 17 or a valve provided at a gas discharge port of the carbon dioxide container 17 is closed, the pressure detected by the pressure meter 45 does not rise properly.

In other words, with the above-described embodiment, even if the power source switch 15a of the gas feeding apparatus 15 is turned on, when the sufficient amount of carbon dioxide is not actually discharged, the operation of the air pump 14a is not stopped.

Modification 1

In the above-described embodiment, when the flow rate adjusting valve 43 is opened and the pressure P in the conduit GP1 exceeds the threshold TH1, the control section 12A immediately transmits the operation stop command to the light source apparatus 14. However, when the pressure P falls to or below the threshold TH1 after exceeding the threshold TH1, or when the pressure P rises to or above a threshold TH1' after exceeding the threshold TH1, the control section 12A may output the operation stop command to the light source apparatus 14 to stop the feeding of the air by the air pump 14a.

Figure 7:
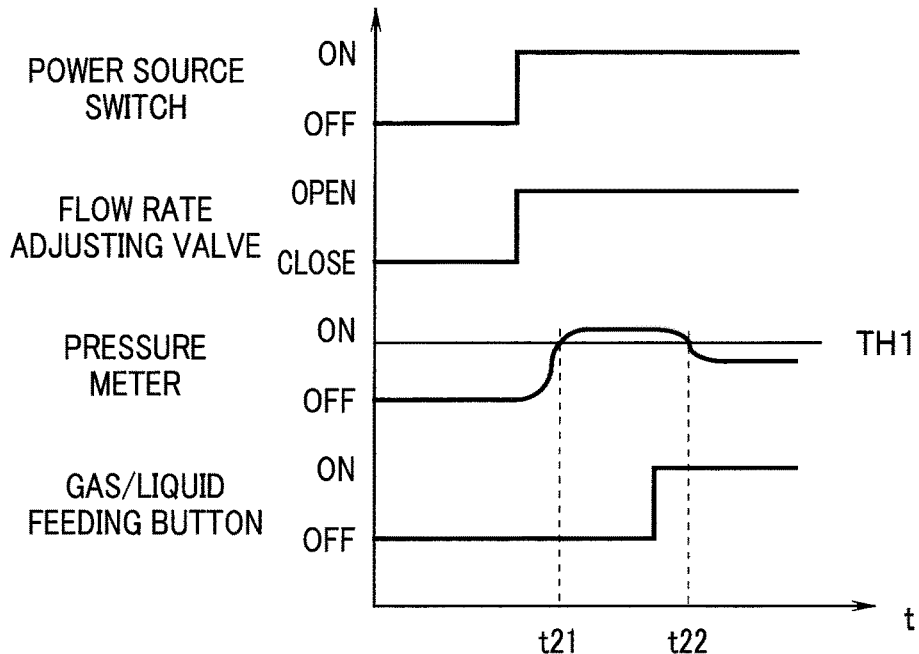
FIG. 7 is a graph showing a state of a power source switch of a gas feeding apparatus, a state of a flow rate adjusting valve, a state of a gas/liquid feeding button, and a change in a pressure detected by a pressure meter, according to a modification 1 of the first embodiment of the present invention.

FIG. 7 is a graph showing the state of the power source switch 15a of the gas feeding apparatus 15, the state of the flow rate adjusting valve 43, the state of the gas/liquid feeding button 22e, and the change in the pressure detected by the pressure meter 45. The horizontal axis in FIG. 7 shows a lapse of time. When the flow rate adjusting valve 43 is opened, the pressure in the conduit GP1 rises. As shown in FIG. 7, the pressure P detected by the pressure meter 45 exceeds the threshold TH1 at time t21. After that, when the operator operates the gas/liquid feeding button 22e, for example, depresses the gas/liquid feeding button 22e to the first stage, the carbon dioxide is discharged from the opening 21b of the nozzle at the distal end of the insertion portion 21. As a result, the pressure P in the conduit GP1 falls to or below the threshold TH1. FIG. 7 shows that the pressure P falls to or below the threshold TH1 at the timing of time t22.

In other words, in the modification 1, if the pressure P detected by the pressure meter 45 exceeds the threshold TH1 and thereafter falls to or below the threshold TH1, the control section 12A transmits the operation stop command for stopping the operation of the air pump 14a to the light source apparatus 14. The modification 1 also provides the same effects as those in the above-described embodiment.

Figure 8:
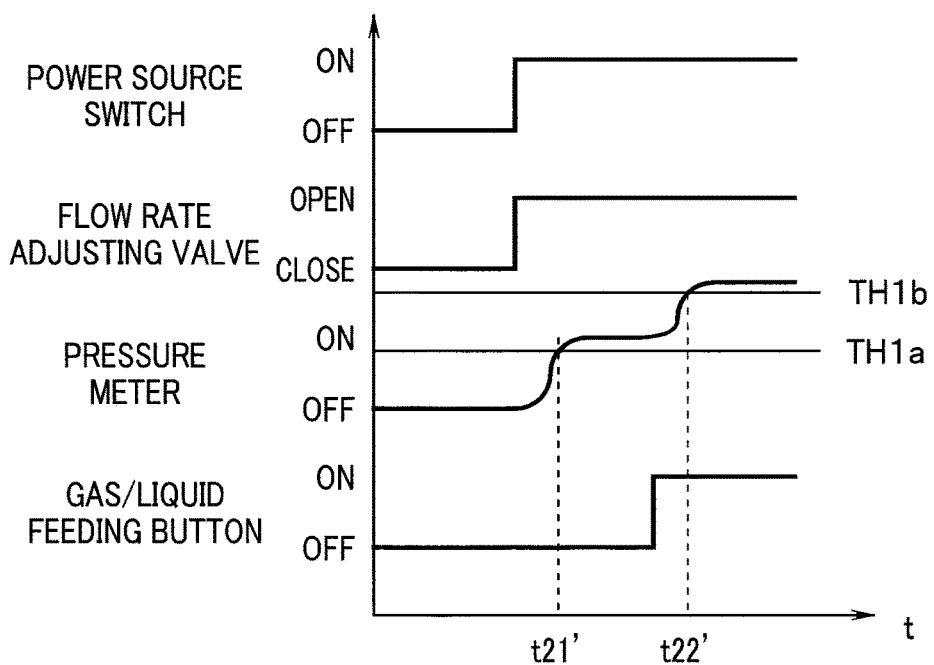
FIG. 8 is a graph showing the state of the power source switch of the gas feeding apparatus, the state of the flow rate adjusting valve, a state of a gas/liquid feeding button, and a change in the pressure detected by the pressure meter, according to the modification 1 of the first embodiment of the present invention.

Description will be made on the case where the gas/liquid feeding button 22c is used. FIG. 8 is a graph showing the state of the power source switch 15a of the gas feeding apparatus 15, the state of the flow rate adjusting valve 43, the state of the gas/liquid feeding button 22c, and the change in the pressure detected by the pressure meter 45. The horizontal axis in FIG. 8 shows a lapse of time. When the flow rate adjusting valve 43 is opened, the pressure in the conduit GP1 rises. As shown in FIG. 8, the pressure P detected by the pressure meter 45 exceeds a threshold TH1a at time t21'. After that, when the operator operates the gas/liquid feeding button 22c, for example, closes the hole of the gas/liquid feeding button 22c, the carbon dioxide is discharged from the opening 21b of the nozzle at the distal end of the insertion portion 21. As a result, the pressure P in the conduit GP1 rises up to a threshold TH1b. This is because an endoscope conduit 21a, which is located on the downstream of the gas/liquid feeding button 22c, has an inner diameter smaller than that of the hole of the gas/liquid feeding button 22c and has a higher flow rate resistance than that of the hole of the gas/liquid feeding button 22c. FIG. 8 shows that the pressure P rises to or above the threshold TH1b at the timing of time t22'.

Thus, in the modification 1 shown in FIG. 8, if the pressure P detected by the pressure meter 45 exceeds the threshold TH1a and thereafter rises to or above the threshold TH1b, the control section 12A transmits the operation stop command for stopping the operation of the air pump 14a to the light source apparatus 14. The modification 1 also provides the same effects as those in the above-described embodiment.

Modification 2

In the above-described modification 1, if the pressure P detected by the pressure meter 45 exceeds the threshold TH1 and thereafter falls to or below the threshold TH1, or if the pressure P exceeds the threshold TH1a and thereafter rises to or above the threshold TH1b, the control section 12A transmits the operation stop command for stopping the operation of the air pump 14a to the light source apparatus 14. However, in the case where the above-described gas feeding switch 15c is in the on-state, if the pressure P detected by the pressure meter 45 exceeds the threshold TH1 and thereafter falls to or below the threshold TH1, or rises to or above the threshold TH1b, the control section 12A may transmit the operation stop command for stopping the operation of the air pump 14a to the light source apparatus 14.

Figure 9:
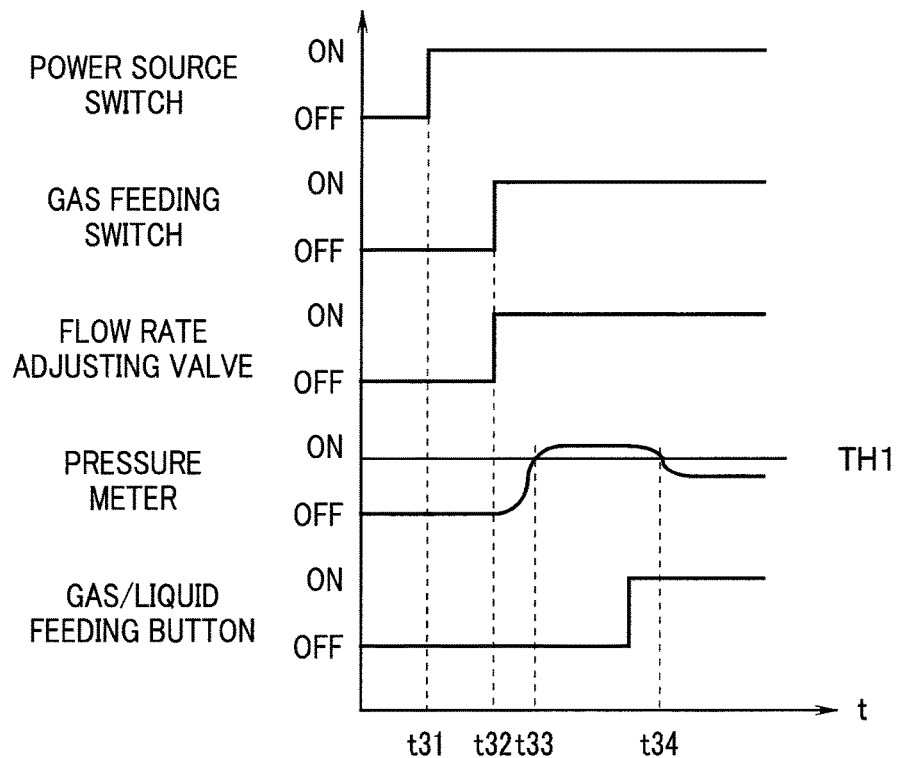
FIG. 9 is a graph showing a state of a power source switch of a gas feeding apparatus, a state of a gas feeding switch, a state of a flow rate adjusting valve, a state of a gas/liquid feeding button, and a change in a pressure detected by a pressure meter, according to a modification 2 of the first embodiment of the present invention.

FIG. 9 is a graph showing the state of the power source switch 15a of the gas feeding apparatus 15, the state of the gas feeding switch 15c, the state of the flow rate adjusting valve 43, the state of the gas/liquid feeding button 22e, and the change in the pressure detected by the pressure meter 45. The horizontal axis in FIG. 9 shows a lapse of time. After the power source switch 15a has been turned on at time t31, when the gas feeding switch 15c is turned on at time t32, the flow rate adjusting valve 43 is opened by the control section 15A. When the flow rate adjusting valve 43 is opened, the pressure P in the conduit GP1 rises. As shown in FIG. 9, the pressure P detected by the pressure meter 45 rises after the time t32, and the pressure P in the conduit GP1 exceeds the threshold TH1.

After that, when the gas/liquid feeding button 22e is depressed to the first stage, gas is fed from the opening 21b of the nozzle at the distal end of the insertion portion 21. As a result, the pressure P in the conduit GP1 falls to or below the threshold TH1. FIG. 9 shows that the pressure P falls to or below the threshold TH1 at the timing of time t34. The modification 2 also provides the same effects as those in the above-described embodiment.

Figure 10:
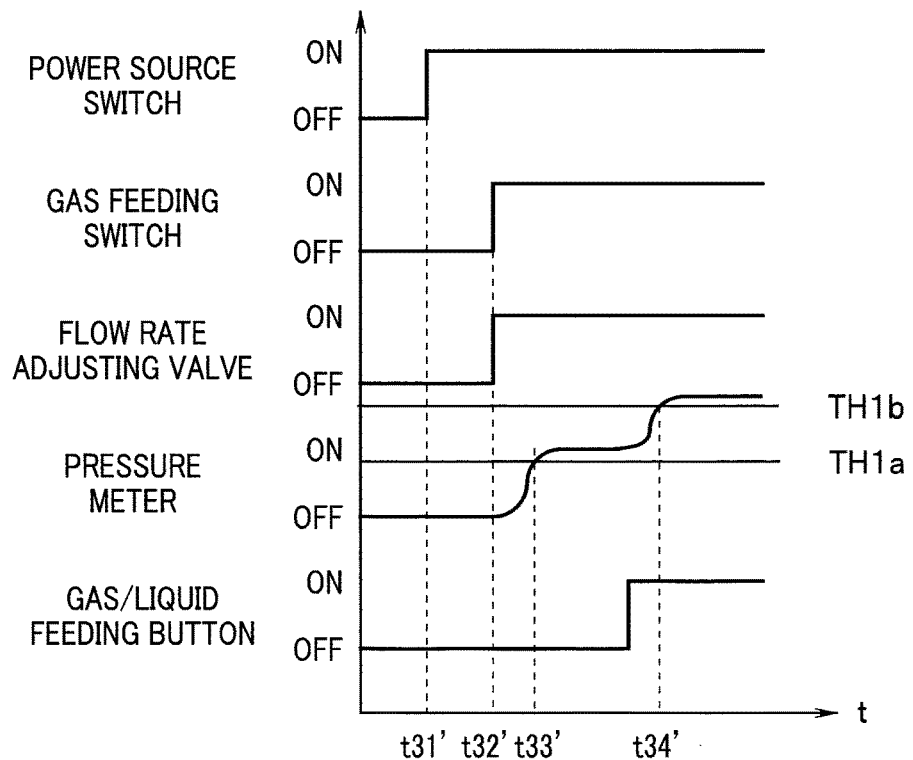
FIG. 10 is a graph showing the state of the power source switch of the gas feeding apparatus, the state of the gas feeding switch, the state of the flow rate adjusting valve, a state of a gas/liquid feeding button, and a change in the pressure detected by the pressure meter, according to the modification 2 of the first embodiment of the present invention.

Description will be made on the case where the gas/liquid feeding button 22c is used. FIG. 10 is a graph showing the state of the power source switch 15a of the gas feeding apparatus 15, the state of the gas feeding switch 15c, the state of the flow rate adjusting valve 43, the state of the gas/liquid feeding button 22c, and the change in the pressure detected by a pressure meter 45. The horizontal axis in FIG. 10 shows a lapse of time. After the power source switch 15a has been turned on at time t31', when the gas feeding switch 15c is turned on at time t32', the flow rate adjusting valve 43 is opened by the control section 15A. When the flow rate adjusting valve 43 is opened, the pressure P in the conduit GP1 rises. As shown in FIG. 10, the pressure P detected by the pressure meter 45 rises after the time t32' and the pressure P in the conduit GP1 exceeds the threshold TH1a.

After that, when the hole of the gas/liquid feeding button 22c is closed, gas is fed from the opening 21b of the nozzle at the distal end of the insertion portion 21. As a result, the pressure P in the conduit GP1 rises to or above the threshold TH1b. FIG. 10 shows that the pressure P rises to or above the threshold TH1b at the timing of time t34'. The modification 2 also provides the same effects as those in the above-described embodiment.

As described above, with the above-described embodiment and the respective modifications, it is possible to provide the endoscope system capable of surely supplying the carbon dioxide into the body cavity while reducing the burden on the operator.

For example, when the gas container is sufficiently filled with carbon dioxide and the valve of the gas container is open, the carbon dioxide can be surely supplied. Therefore, the air pump is brought into the non-operating state. However, when the gas container is not sufficiently filled with carbon dioxide or the valve of the gas container is closed, the carbon dioxide cannot be supplied. Therefore, the supply of the air is continued without being stopped, and the gas is continuously supplied into the body cavity.

Second Embodiment

In the first embodiment, the pressure in the conduit GP1 located on the downstream of the flow rate adjusting valve 43 is detected, and the operation of the air pump 14a of the light source apparatus 14 is stopped. In contrast, in the second embodiment, the flow rate of the gas flowing through the conduit GP is detected and the operation of the air pump 14a of the light source apparatus 14 is stopped.

A configuration of a medical system according to the present embodiment is substantially the same as the configuration of the medical system 1 according to the first embodiment as shown in FIGS. 1 and 2. The same constituent elements will be described by using the same reference signs and detailed description thereof will be omitted.

Figure 11:
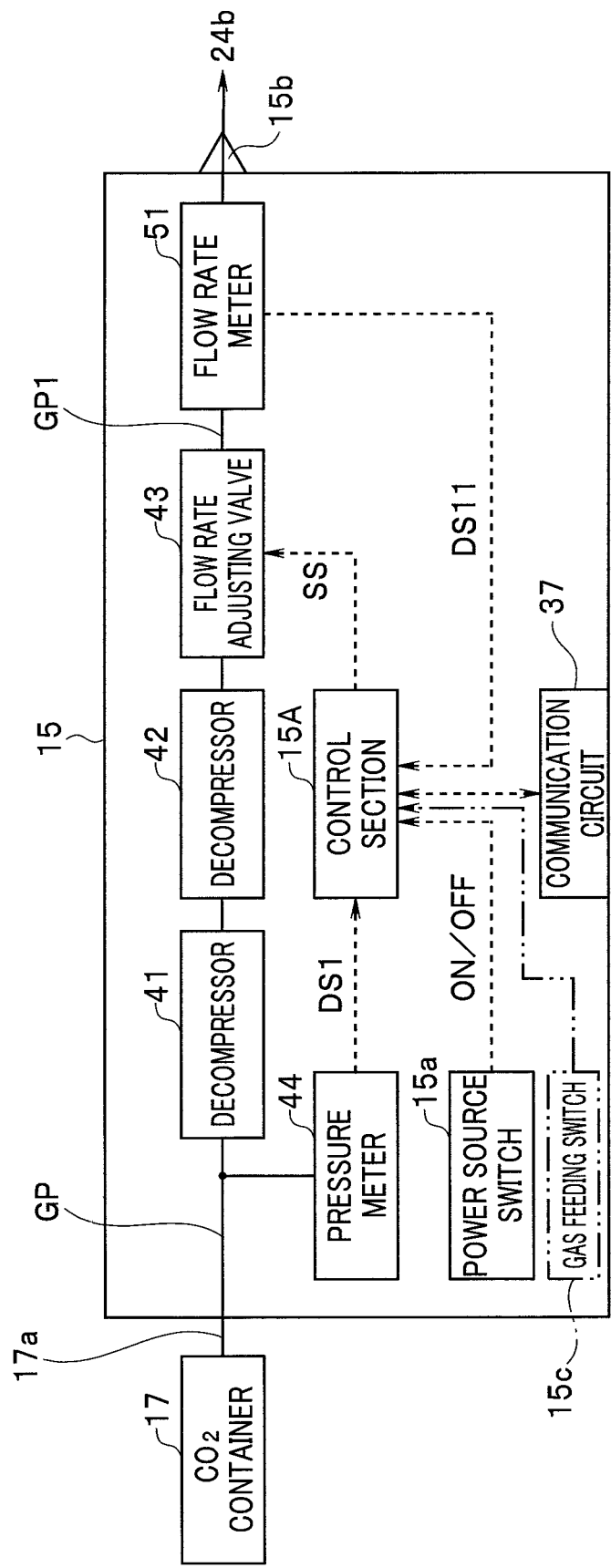
FIG. 11 is a block diagram showing a configuration of a gas feeding apparatus according to a second embodiment of the present invention.

FIG. 11 is a block diagram showing the configuration of the gas feeding apparatus 15 according to the second embodiment. The configuration of the gas feeding apparatus 15 is substantially the same as that of the gas feeding apparatus 15 in the first embodiment. The same constituent elements are attached with the same reference signs and description thereof will be omitted. Only the different constituent elements will be described.

The conduit GP1 is provided with a flow rate meter 51. The flow rate meter 51 is configured to detect the flow rate of the gas flowing through the conduit GP1, and outputs, to the control section 15A, a detection signal DS11 of the flow rate as the detected state of the gas. In other words, the flow rate meter 51 is provided inside the gas feeding apparatus 15, and configures a gas state detector configured to detect the state of the carbon dioxide, i.e., the flow rate in the present embodiment. The flow rate meter 51 as the gas state detector is provided in the post-stage of the flow rate adjusting valve 43 configured to adjust the flow rate of the carbon dioxide to be fed from the gas feeding apparatus 15.

The detection signal DS11 is transmitted from the control section 15A to the control section 12A. The control section 12A executes the stop control of the air pump, which is shown in FIG. 4, based on flow rate data which the control section 12A receives in real time.

Figure 12:
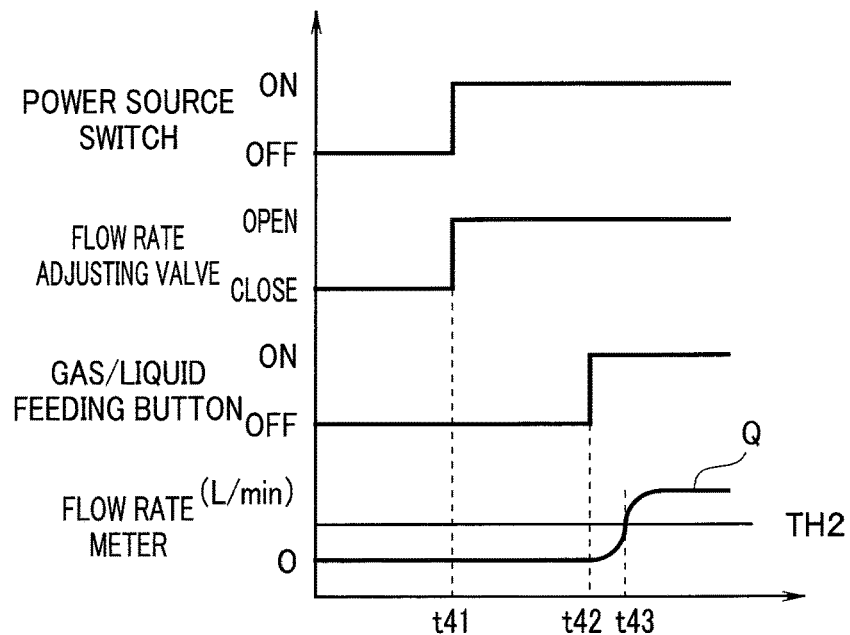
FIG. 12 is a graph showing a state of a power source switch of the gas feeding apparatus, a state of a flow rate adjusting valve, a state of a gas/liquid feeding button, and a change in a flow rate detected by a flow rate meter, according to the second embodiment of the present invention.

FIG. 12 is a graph showing the state of the power source switch 15a of the gas feeding apparatus 15, the state of the flow rate adjusting valve 43, the state of the gas/liquid feeding button 22e, and a change in the flow rate detected by the flow rate meter 51. The horizontal axis in FIG. 12 shows a lapse of time. When the power source switch 15a is turned on at time t41, the flow rate adjusting valve 43 is opened by the control section 15A.

After the flow rate adjusting valve 43 has been opened, when the gas/liquid feeding button 22e is operated at time t42 and gas feeding is performed, the carbon dioxide flows through the conduit GP1. As shown in FIG. 12, a flow rate Q of the carbon dioxide, which is detected by the flow rate meter 51, rises after the time t42.

The control section 15A of the gas feeding apparatus 15 transmits, in real time, detection value data of the detection signal DS11 to the system controller 12 through the communication circuit 37. Accordingly, the control section 12A of the system controller 12 constantly monitors the received detection value data.

In the S2, the control section 12A determines, based on the received detection value data, whether the flow rate Q of the carbon dioxide in the conduit GP1 exceeds a predetermined threshold TH2. The threshold TH2 is a flow rate value of a level at which it can be determined that the flow of the carbon dioxide of a certain level or more occurs, after the start of the feeding of the gas by the gas/liquid feeding button 22e having been depressed to the first stage. The operator inputs, in advance, the threshold TH2 from the setting section 12C, to set the threshold TH2. The threshold TH2 is stored in the data storage region of the storage apparatus 12B.

The control section 12A determines, based on the received detection value data, whether the flow rate Q of the carbon dioxide in the conduit GP1 exceeds the predetermined threshold TH2. When detecting that the flow rate Q of the carbon dioxide exceeds the predetermined threshold TH2, the control section 12A transmits the operation stop command for stopping the operation of the air pump 14a to the light source apparatus 14. FIG. 12 shows that the flow rate Q of the carbon dioxide in the conduit GP1 exceeds the predetermined threshold TH2 at the timing of time 43. When receiving the operation stop command, the light source apparatus 14 stops the operation of the air pump 14a As described above, when determining that the state of the carbon dioxide detected by the flow rate meter 51, i.e., the flow rate in the present embodiment, exceeds the predetermined threshold TH2, the control section 12A performs the control for stopping the feeding of the air by the air pump 14a.

Figure 13:
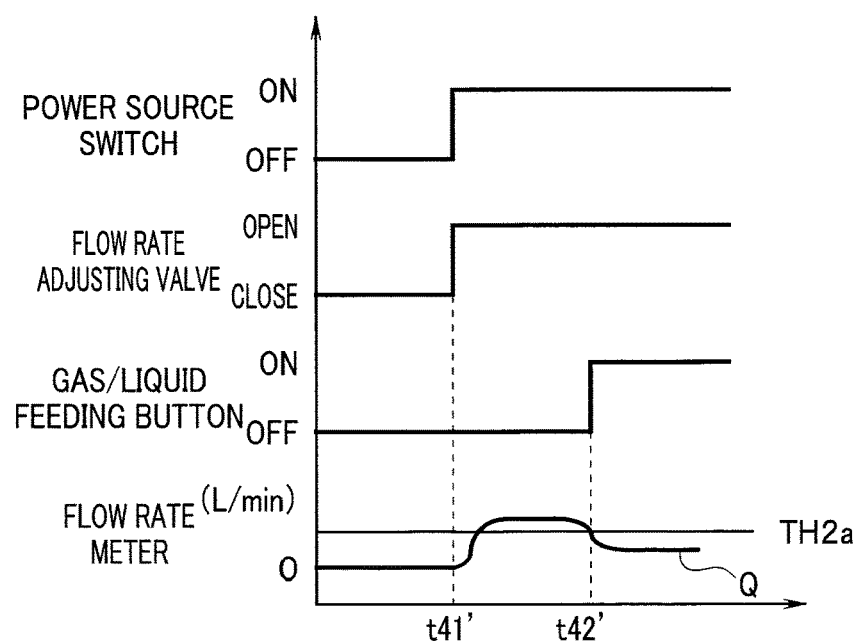
FIG. 13 is a graph showing the state of the power source switch of the gas feeding apparatus, the state of the flow rate adjusting valve, a state of a gas/liquid feeding button, and a change in the flow rate detected by the flow rate meter, according to the second embodiment of the present invention.

Description will be made on the case where the gas/liquid feeding button 22c is used. FIG. 13 is a graph showing the state of the power source switch 15a of the gas feeding apparatus 15, the state of the flow rate adjusting valve 43, the state of the gas/liquid feeding button 22c, and the change in the flow rate detected by the flow rate meter 51. The horizontal axis in FIG. 13 shows a lapse of time. When the power source switch 15a is turned on at time t41', the flow rate adjusting valve 43 is opened by the control section 15A. Since this causes the gas to be leaked out from the hole of the gas/liquid feeding button, the flow rate detected by the flow rate meter starts to rise at the time t41' and after a certain time elapses, the flow rate is stabilized to a constant value.

After the flow rate adjusting valve 43 has been opened, when the gas/liquid feeding button 22c is operated at time t42' and gas feeding is performed, the flow rate of the carbon dioxide flowing through the conduit GP1 falls. As shown in FIG. 13, the flow rate Q of the carbon dioxide detected by the flow rate meter 51 decreases below a threshold TH2a after the time t42'.

The control section 15A of the gas feeding apparatus 15 transmits, in real time, the detection value data of the detection signal DS11 to the system controller 12 through the communication circuit 37. Accordingly, the control section 12A of the system controller 12 constantly monitors the received detection value data.

In the S2, the control section 12A determines, based on the received detection value data, whether the flow rate Q of the carbon dioxide in the conduit GP1 exceeds the predetermined threshold TH2a and thereafter decreases below the threshold TH2a. The threshold TH2a is a flow rate value of a level at which it can be determined that the flow of the carbon dioxide of a certain level or more occurs, after the start of the feeding of the gas. The operator inputs, in advance, the threshold TH2a from the setting section 12C, to set the threshold TH2a. The threshold TH2a is stored in the data storage region of the storage apparatus 12B.

The control section 12A determines, based on the received detection value data, whether the flow rate Q of the carbon dioxide in the conduit GP1 exceeds the predetermined threshold TH2a and thereafter decreases below the threshold TH2a. When detecting that the flow rate Q of the carbon dioxide exceeds the predetermined threshold TH2a and thereafter decreases below the threshold TH2a, the control section 12A transmits the operation stop command for stopping the operation of the air pump 14a to the light source apparatus 14. FIG. 13 shows that the flow rate Q of the carbon dioxide in the conduit GP1 exceeds the predetermined threshold TH2a at the timing after the time t41' and the flow rate Q of the carbon dioxide in the conduit GP1 falls below the predetermined threshold TH2a at the timing after the time t42'. When receiving the operation stop command, the light source apparatus 14 stops the operation of the air pump 14a. As described above, when determining that the state of the gas detected by the flow rate meter 51, i.e., the flow rate in the present embodiment, exceeds the predetermined threshold TH2a and thereafter falls below the predetermined threshold TH2a, the control section 12A performs the control for stopping the feeding of the air by the air pump 14a.

In the case where the light source apparatus 14 includes an on/off switch for turning on and off the air pump 14a, if the air pump 14a is operated when the light source apparatus 14 receives the operation stop command, the control section 14A stops the operation of the air pump 14a. If the air pump 14a is not operated when the light source apparatus 14 receives the operation stop command, the control section 14A does nothing.

Furthermore, also in the present embodiment, similarly as in the first embodiment, in the case where the air pump 14a is not operated when the light source apparatus 14 receives the operation stop command, the control section 14A may bring the light source apparatus 14 into the operation inhibited state in which the air pump 14a is not allowed to operate even if the on/off switch is turned on later. In other words, the light source apparatus 14 is brought into the state which does not accept the turning on of the on/off switch. When the light source apparatus 14 is in the operation inhibited state, the operator may be caused to perform an operation for confirming that the air pump 14a is allowed to operate so that the operator can bring the air pump 14a from the operation inhibited state into the operation enabled state in a case where the carbon dioxide concentration in the blood of the patient rises, for example.

As described above, with the above-described embodiments and the respective modifications, it is possible to provide the endoscope system capable of surely supplying the carbon dioxide into the body cavity while reducing the burden on the operator.

For example, when the gas container is sufficiently filled with carbon dioxide and the valve of the gas container is open, the carbon dioxide can be surely supplied. Therefore, the air pump is brought into the non-operating state. However, when the gas container is not sufficiently filled with carbon dioxide or the valve of the gas container is closed, the carbon dioxide cannot be supplied. Therefore, the supply of the air is continued without being stopped, and the gas is continuously supplied into the body cavity.

Note that, also in the present embodiment, the control section 12A receives the detection signal of the flow rate meter 51 from the gas feeding apparatus 15, to transmit a stop signal for stopping the operation of the air pump 14a to the light source apparatus 14. However, the control section 15A of the gas feeding apparatus 15 may transmit the stop signal directly to the light source apparatus 14.

Furthermore, the control section 14A of the light source apparatus 14 may receive the detection value data of the flow rate meter 51 from the gas feeding apparatus 15, to determine whether the flow rate exceeds the threshold TH2, and may stop the operation of the air pump 14a.

In addition, in the present embodiment, after turning on the power source switch 15a (or gas feeding switch) of the gas feeding apparatus 15, the operator operates the gas/liquid feeding button 22c, to thereby allow the carbon dioxide to flow actually. Then, detection is made on whether the flow rate Q of the carbon dioxide actually exceeds the predetermined threshold TH2. If the valve of the carbon dioxide container 17 is closed, or the remaining amount of the carbon dioxide in the carbon dioxide container 17 is small, the carbon dioxide does not flow to the conduit GP1. In that case, the air pump 14a is not stopped. Therefore, the operator can secure the field of view without being obstructed, and continue the examination and the like.

Also in the present embodiment, similarly as in the first embodiment or the modification 1, if the above-described power source switch 15a or the gas feeding switch 15c is turned on and the flow rate Q detected by the flow rate meter 51 exceeds the threshold TH2, the control section 12A may transmit the operation stop command for stopping the operation of the air pump 14a. In other words, when the state of the carbon dioxide, i.e., the flow rate in the present embodiment exceeds the predetermined threshold TH2 and the gas feeding switch 15c of the gas feeding apparatus 15 is in the on-state, the control section 12A performs the control for stopping the feeding of the air by the air pump 14a. The control section 12A can determine whether the power source switch 15a or the gas feeding switch 15c of the gas feeding apparatus 15 is in the on-state, by trying to perform communication with the gas feeding apparatus 15 to confirm whether communication is available. The control section 12A can determine that the gas feeding switch 15c of the gas feeding apparatus 15 is turned on by performing communication with the gas feeding apparatus 15 to acquire information on the state of the gas feeding switch 15c via the communication.

Third Embodiment

In the first embodiment, the pressure in the conduit GP1 located on the downstream of the flow rate adjusting valve 43 is detected, to stop the operation of the air pump 14a of the light source apparatus 14. In contrast, in the third embodiment, a concentration of the carbon dioxide flowing through the conduit GP1 is detected, to stop the operation of the air pump 14a of the light source apparatus 14.

A configuration of a medical system of the present embodiment is substantially the same as the configuration of the medical system 1 of the first embodiment as shown in FIGS. 1 and 2. The same constituent elements are attached with the same reference signs and detailed description thereof will be omitted.

Figure 14:
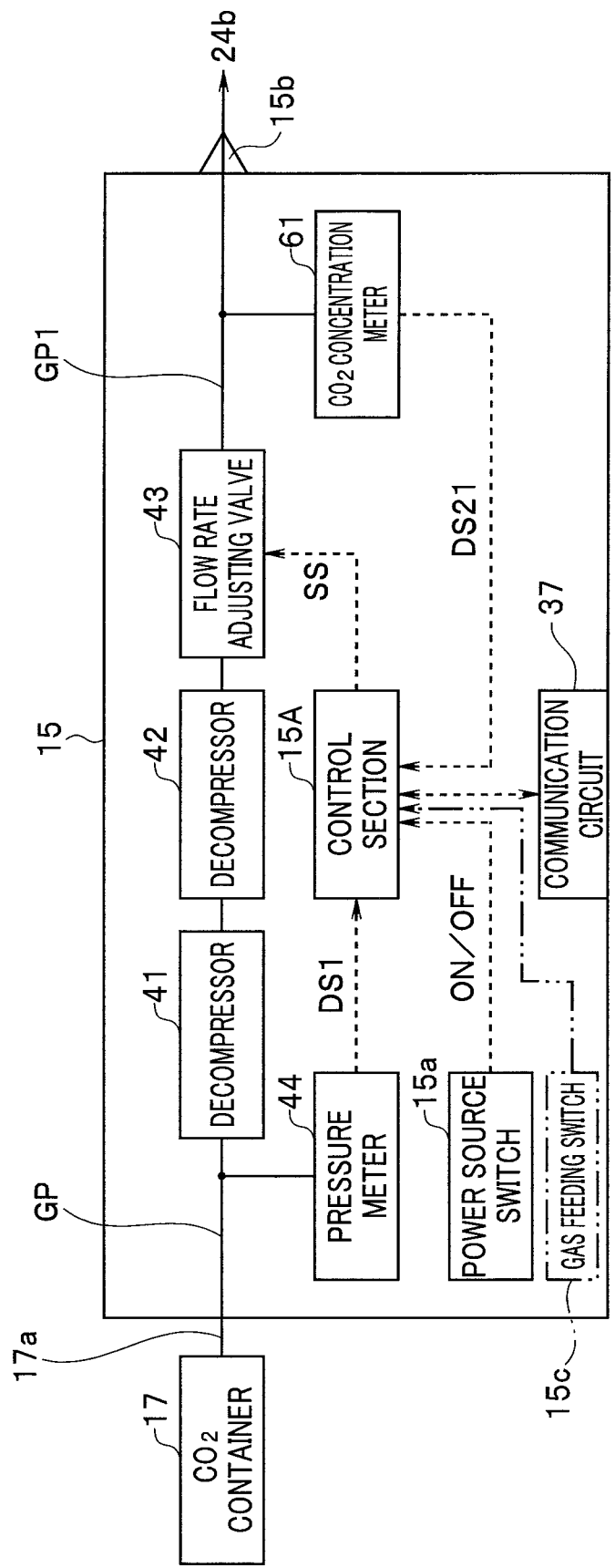
FIG. 14 is a block diagram showing a configuration of a gas feeding apparatus according to a third embodiment of the present invention.

FIG. 14 is a block diagram showing the configuration of the gas feeding apparatus 15 according to the third embodiment. The configuration of the gas feeding apparatus 15 is substantially the same as that of the gas feeding apparatus 15 of the first embodiment. The same constituent elements are attached with the same reference signs and description thereof will be omitted. Only the different constituent elements will be described.

The conduit GP1 is provided with a carbon dioxide concentration meter 61. The carbon dioxide concentration meter 61 is configured to detect the carbon dioxide concentration of the gas flowing through the conduit GP1, and outputs, to the control section 15A, a detection signal DS21 of the carbon dioxide concentration as the detected state of the gas. In other words, the carbon dioxide concentration meter 61 is provided inside the gas feeding apparatus 15, and configures a gas state detector configured to detect the state of the carbon dioxide, i.e., the carbon dioxide concentration in the present embodiment. The carbon dioxide concentration meter 61 as the gas state detector is provided in the post-stage of the flow rate adjusting valve 43 configured to adjust the flow rate of the carbon dioxide to be fed from the gas feeding apparatus 15.

The detection signal DS21 is transmitted from the control section 15A to the control section 12A. The control section 12A executes the stop control of the air pump, which is shown in FIG. 4, based on carbon dioxide concentration data which the control section 12A receives in real time.

Figure 15:
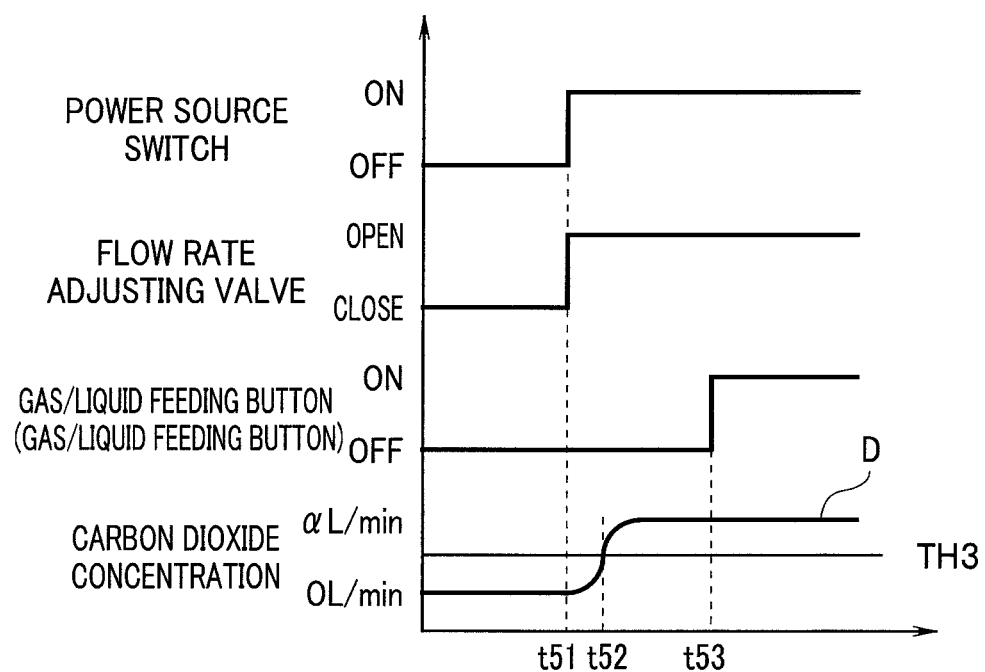
FIG. 15 is a graph showing a state of a power source switch of the gas feeding apparatus, a state of a flow rate adjusting valve, a state of a gas/liquid feeding button, and a change in a carbon dioxide concentration detected by a carbon dioxide concentration meter, according to the third embodiment of the present invention.

FIG. 15 is a graph showing the state of the power source switch 15a of the gas feeding apparatus 15, the state of the flow rate adjusting valve 43, the state of the gas/liquid feeding button 22c (or gas/liquid feeding button 22e), and a change in the carbon dioxide concentration detected by the carbon dioxide concentration meter 61. The horizontal axis in FIG. 15 shows a lapse of time. When the power source switch 15a is turned on at time t51, the flow rate adjusting valve 43 is opened by the control section 15A.

After the flow rate adjusting valve 43 has been opened, the carbon dioxide flows into the conduit GP1, regardless of whether the gas/liquid feeding button 22c is operated. As shown in FIG. 15, a carbon dioxide concentration D detected by the carbon dioxide concentration meter 61 rises after the time t51. Since the gas is leaked out from the hole of the gas/liquid feeding button 22c, the carbon dioxide concentration D starts to rise at the time t51, and after a certain time elapses, the carbon dioxide concentration is stabilized to a constant value above a threshold TH3.

The control section 15A of the gas feeding apparatus 15 transmits, in real time, detection value data of the detection signal DS21 to the system controller 12 through the communication circuit 37. Accordingly, the control section 12A of the system controller 12 constantly monitors the received detection value data.

In the S2, the control section 12A determines, based on the received detection value data, whether the carbon dioxide concentration D in the conduit GP1 exceeds the predetermined threshold TH3. The operator inputs, in advance, the threshold TH3 from the setting section 12C, to set the threshold TH3. The threshold TH3 is stored in the data storage region of the storage apparatus 12B.

The control section 12A determines, based on the received detection value data, whether the carbon dioxide concentration D in the conduit GP1 exceeds the predetermined threshold TH3. When detecting that the carbon dioxide concentration D exceeds the predetermined threshold TH3, the control section 12A transmits the operation stop command for stopping the operation of the air pump 14a to the light source apparatus 14. FIG. 15 shows that the carbon dioxide concentration D in the conduit GP1 exceeds the predetermined threshold TH3 at the timing of time t52. In the example shown in FIG. 15, the gas/liquid feeding button 22c (or the gas/liquid feeding button 22e) is operated at the timing of time t53. When receiving the operation stop command, the light source apparatus 14 stops the operation of the air pump 14a. As described above, when determining that the state of the carbon dioxide detected by the carbon dioxide concentration meter 61, i.e., the carbon dioxide concentration in the present embodiment, exceeds the predetermined threshold TH3, the control section 12A performs the control for stopping the feeding of the air by the air pump 14a.

Note that, also in the present embodiment, the control section 12A receives the detection signal of the carbon dioxide concentration meter 61 from the gas feeding apparatus 15, to transmit the operation stop command for stopping the operation of the air pump 14a to the light source apparatus 14. However, the control section 15A of the gas feeding apparatus 15 may transmit the operation stop command directly to the light source apparatus 14.

Furthermore, the control section 14A of the light source apparatus 14 may receive the detection value data of the carbon dioxide concentration meter 61 from the gas feeding apparatus 15, to determine whether the carbon dioxide concentration exceeds the threshold TH3, and may stop the operation of the air pump 14a.

In addition, in the present embodiment, after turning on the power source switch 15a (or gas feeding switch) of the gas feeding apparatus 15, the operator operates the gas/liquid feeding button 22c (or the gas/liquid feeding button 22e), to thereby allow the carbon dioxide to flow actually.

Then, detection is made on whether the carbon dioxide concentration D actually exceeds the predetermined threshold TH3. If the valve of the carbon dioxide container 17 is closed, or the remaining amount of the carbon dioxide in the carbon dioxide container 17 is small, the carbon dioxide does not flow to the conduit GP1, and the carbon dioxide concentration D does not rise. In that case, the air pump 14a is not stopped. Therefore, the operator can secure the field of view without being obstructed, and continue the examination and the like.

Also in the present embodiment, similarly as in the first embodiment or the modification 1, when the above-described power source switch 15a or the gas feeding switch 15c is turned on and the carbon dioxide concentration D detected by the carbon dioxide concentration meter 61 exceeds the threshold TH3, the control section 12A may transmit the operation stop command for stopping the operation of the air pump 14a. In other words, when the state of the carbon dioxide, i.e., the carbon dioxide concentration in the present embodiment exceeds the predetermined threshold TH3 and the gas feeding switch 15c of the gas feeding apparatus 15 is in the on-state, the control section 12A performs the control for stopping the feeding of the air by the air pump 14a. The control section 12A can determine whether the power source switch 15a or the gas feeding switch 15c of the gas feeding apparatus 15 is in the on-state by trying to perform communication with the gas feeding apparatus 15 to confirm whether communication is available. The control section 12A can determine that the gas feeding switch 15c of the gas feeding apparatus 15 is turned on by performing communication with the gas feeding apparatus 15 to acquire information on the state of the gas feeding switch 15c via the communication.

As described above, with the above-described embodiments and the respective modifications, it is possible to provide the endoscope system capable of surely supplying the carbon dioxide into the body cavity while reducing the burden on the operator.

For example, when the gas container is sufficiently filled with carbon dioxide and the valve of the gas container is open, the carbon dioxide can be surely supplied. Therefore, the air pump is brought into the non-operating state. However, when the gas container is not sufficiently filled with carbon dioxide or the valve of the gas container is closed, the carbon dioxide cannot be supplied. Therefore, the supply of air is continued without being stopped, and the gas is continuously supplied into the body cavity.

In the above-described embodiments and the respective modifications, any one of the pressure, the flow rate, and the carbon dioxide concentration of the carbon dioxide in the conduit is detected by one of the detectors. However, at least two or more states of the carbon dioxide, for example, the pressure and the flow rate, the pressure and the carbon dioxide concentration, the flow rate and the carbon dioxide concentration, or the pressure, the flow rate, and the carbon dioxide concentration may be detected, and if even at least one of the states exceeds a predetermined threshold, the air pump 14a of the light source apparatus 14 may be stopped.

The present invention is not limited to the above-described embodiments, but various changes, modifications, and the like are possible without changing the gist of the present invention.

What is claimed is:

1. An endoscope system comprising:
   a gas supplying apparatus configured to supply carbon dioxide, the gas supplying apparatus comprising:

a gas state sensor configured to detect a state of the carbon dioxide;
an air supplying apparatus comprising a pump configured to supply air; and
a processor comprising hardware, the processor configured to control the air supplying apparatus to stop supplying the air when the processor determines that the state of the carbon dioxide detected by the gas state sensor reaches a predetermined threshold during a period in which the carbon dioxide and the air are supplied simultaneously.

2. The endoscope system according to claim 1, wherein the gas state sensor is a pressure meter.

3. The endoscope system according to claim 2, wherein the processor is configured to stop the supplying of the air by the air supplying apparatus, when a pressure detected by the pressure meter exceeds the predetermined threshold and a gas supplying switch of the gas supplying apparatus is on.

4. The endoscope system according to claim 2, wherein the processor is configured to perform the control for stopping the supplying of the air by the air supplying apparatus, when a pressure detected by the pressure meter falls to or below the predetermined threshold after exceeding the predetermined threshold.

5. The endoscope system according to claim 2, wherein the processor is configured to perform the control for stopping the supplying of the air by the air supplying apparatus, when a pressure detected by the pressure meter rises to or above another threshold higher than the predetermined threshold after exceeding the predetermined threshold.

6. The endoscope system according to claim 1, wherein the gas state sensor is a flow rate meter.

7. The endoscope system according to claim 6, wherein the flow rate meter is provided downstream of a flow rate adjusting valve, the flow rate adjusting valve being configured to adjust a flow rate of the carbon dioxide supplied from the gas supplying apparatus.

8. The endoscope system according to claim 7, wherein the processor is configured to perform the control for stopping the supplying of the air by the air supplying apparatus, when the flow rate detected by the flow rate meter exceeds the predetermined threshold and a gas supplying switch of the gas supplying apparatus is on.

9. The endoscope system according to claim 1, wherein the gas state sensor is a carbon dioxide concentration meter.

10. The endoscope system according to claim 9, wherein the carbon dioxide concentration meter is provided downstream of a flow rate adjusting valve, the flow rate adjusting valve being configured to adjust a flow rate of the carbon dioxide to be fed from the gas supplying apparatus.

11. The endoscope system according to claim 10, wherein the processor is configured to perform the control for stopping the supplying of the air by the air supplying apparatus, when a carbon dioxide concentration detected by the carbon dioxide concentration meter exceeds the predetermined threshold and a gas supplying switch of the gas supplying apparatus is on.

12. The endoscope system according to claim 1, wherein the gas state sensor includes at least two of a pressure meter, a flow rate meter, and a carbon dioxide concentration meter that are provided downstream of a flow rate adjusting valve, the flow rate adjusting valve being configured to adjust a flow rate of the carbon dioxide to be fed from the gas supplying apparatus, and
the state of the carbon dioxide includes at least two of a pressure, a flow rate and a carbon dioxide concentration of the carbon dioxide is a conduit located downstream of the flow rate adjusting valve, the at least two of the pressure, the flow rate, and the carbon dioxide concentration being detected respectively by at least two of the pressure meter, the flow rate meter, and the carbon dioxide concentration meter.

13. The endoscope system according to claim 1, further comprising a threshold setting apparatus configured to set the predetermined threshold for the state of the carbon dioxide.

14. The endoscope system according to claim 1, wherein a nozzle disposed at a distal end of an endoscope is configured to discharge the carbon dioxide or the air when an operation portion of the endoscope is operated.

15. The endoscope system according to claim 1, further comprising:
a decompressor configured to decompress the carbon dioxide; and
a valve configured to supply the decompressed carbon dioxide,
wherein the gas state sensor is disposed downstream of each of the decompressor and the valve.

16. The endoscope system according to claim 1, wherein the gas supplying apparatus further comprising a flow rate adjusting valve configured to adjust a flow rate of the carbon dioxide from the gas supplying apparatus,
wherein the gas state sensor is provided downstream of the flow rate adjusting valve.

17. The endoscope system according to claim 16, wherein the gas supplying apparatus further comprising a controller configured to perform the adjustment of the flow rate adjusting valve.

18. An endoscope system comprising:
a gas supplying apparatus configured to supply carbon dioxide, the gas supplying apparatus comprising:
a gas state sensor configured to detect a state of the carbon dioxide;
an air supplying apparatus comprising a pump configured to supply air; and
a processor comprising hardware, wherein when the gas supplying apparatus is turned on, the processor is configured to:
controlling the pump to supply air;
controlling the gas supplying apparatus to supply carbon dioxide such that the air and carbon dioxide are supplied simultaneously;
receive the state of the carbon dioxide from the gas state sensor,
controlling the pump to stop supplying the air when the state of the supplied carbon dioxide reaches a predetermined threshold, and
subsequent to the stopping, set the air supplying apparatus in an operation inhibited state in which the pump is not allowed to operate.

* * * * *